United States Patent [19]

Cusack et al.

[11] Patent Number: 5,180,749
[45] Date of Patent: Jan. 19, 1993

[54] ANTIMICROBIAL COMPOSITION

[75] Inventors: Timothy M. Cusack, Wallington; Vincent J. Sickora, Roseland; Robert W. Bender, Jersey City, all of N.J.

[73] Assignee: Sterling Winthrop, Inc., New York, N.Y.

[21] Appl. No.: 396,875

[22] Filed: Aug. 22, 1989

[51] Int. Cl.$^5$ .................. A01N 33/18; A01N 33/24
[52] U.S. Cl. .................. 514/726; 514/724; 514/730; 514/760; 424/406; 424/405
[58] Field of Search .......... 514/399, 108, 274, 737, 514/724, 730, 726, 762; 546/15; 424/406, 405

[56] References Cited

U.S. PATENT DOCUMENTS 4,336,270  6/1982  Muntwyler ................. 514/737
4,446,153  5/1984  Yang ........................ 424/343
4,695,453  9/1987  Tuominen et al. ........... 424/81

FOREIGN PATENT DOCUMENTS 3117792  11/1982  Fed. Rep. of Germany.
0154102   9/1982  Japan.

Primary Examiner—Jose G. Dees
Assistant Examiner—Deborah D. Carr
Attorney, Agent, or Firm—John R. Everett

[57] ABSTRACT

An aqueous antimicrobial composition comprising from about 10 to about 30 percent by weight of ethyl alcohol, from about 2 to about 5 percent by weight of benzyl alcohol and the remainder to 100% water, and a method of use of the composition for destroying or reducing the number of microbes on a surface contaminated therewith.

18 Claims, No Drawings

ANTIMICROBIAL COMPOSITION

BACKGROUND OF THE INVENTION

(a) Field of the Invention

The invention relates to aqueous ethanolic antimicrobial compositions for treating surfaces so as to render them essentially free of harmful microbial contamination or reduce the level of harmful microbial contamination thereon.

(b) Information Disclosure Statement

It is well known that ethyl alcohol, in combination with water, at concentrations of 50–90% provides broad spectrum germicidal activity. Aqueous ethyl alcohol (70%) is also known to be virucidal against lipophilic and some hydrophilic viruses. Hard surface disinfectant compositions based on aqueous ethyl alcohol also are known. For example, a current commercially available hard surface disinfectant product based on ethyl alcohol contains as active ingredients 79% ethyl alcohol and 0.1% o-phenylphenol, minor amounts of inert ingredients, and the balance water. This product, when applied to environmental surfaces, kills staph and strep germs, athlete's foot fungus, hydrophilic viruses such as rhino-39, and lipophilic viruses such as influenza A2 (Japan), influenza type B, herpes simplex 1, adeno type 2 and vaccinia.

Benzyl alcohol is known to possess antibacterial and antifungal activities. Furthermore, U.S. Pat. No. 4,200,655 discloses that benzyl alcohol possesses virucidal activity when tested against three strains of human rhinovirus, herpes simplex virus types 1 and 2 and two strains of influenza virus in suspension at concentrations in the range of from 1.5 to 6% and that compositions containing benzyl alcohol as active ingredient are intended for topical virucidal use both in vivo and in vitro, especially for use on the hands and especially for preventing transmission of rhinoviruses.

Chemical Abstracts 66: 44357p (1967) discloses the inhibitory effect of benzyl alcohol on the multiplication of SV-40, vaccinia and herpes simplex viruses at concentrations of 9–14 mM.

U.S. Pat. No. 4,446,153 discloses a skin sanitizing composition particularly suited as a teat dip or udder wash for dairy cows comprising at least one phenyl alkanol such as benzyl alcohol as the microbicidal or sanitizing ingredient. Aqueous compositions containing 1 and 4% benzyl alcohol are exemplified.

U.S. Pat. No. 4,695,453 discloses thickened alcoholic antibacterial compositions containing one or more alcohols having antibacterial activity and that the compositions preferably contain ethanol, propanol and benzyl alcohol as the active ingredients. The preferred compositions preferably contain a major portion (between about 40 and about 50% by weight) of ethanol which contains 4% water, a minor portion (between about 20% and 30% by weight) of anhydrous isopropanol, and a nominal amount (about 0.5% to about 2% by weight) of benzyl alcohol. This patent refers to a commercial antibacterial product named Spitacid ® available from Henkel comprising approximately 46% by weight ethanol (containing about 4% water), 27% anhydrous isopropanol, 1% benzyl alcohol and the balance water.

German Offenlegungsschrift No. 3,117,792 discloses virucidal compositions for disinfecting the skin, hands, surfaces and instruments comprising aqueous solutions containing 3 to 55% by weight of mono- or polyhydroxy aliphatic alcohols with up to 8 carbon atoms in the aliphatic chain, 0.1 to 5% by weight of phenol or substituted phenols and 2 to 40% by weight of an anionic, cationic, nonionic or amphoteric surfactant. A composition is exemplified which contains 78.0% ethanol, 2.0% benzyl alcohol, 2.5% 4-chloro-2-benzylphenol, 0.15% 2-hydroxytrichlorodiphenyl ether, 6.0% benzalkonium chloride, 3.0% alkylamine oxide and the balance perfume and water.

SUMMARY OF THE INVENTION

The present invention resulted from a project undertaken to develop an antimicrobial composition based on aqueous ethyl alcohol in which water is preponderant with the primary emphasis on such a composition useful as a disinfectant for hard, nonporous surfaces. In pursuing this project, compositions comprising water as the major component and containing combinations of ethyl alcohol and benzyl alcohol were investigated and found not only to possess good antimicrobial activity but also to exhibit synergistic antimicrobial activity with respect to particular pathogenic organisms as more fully discussed herein below.

Thus this invention provides an aqueous antimicrobial composition comprising from about 10 to about 30 percent by weight of ethyl alcohol, from about 2 to about 5 percent by weight of benzyl alcohol and the remainder to 100 percent water.

The compositions of the invention are useful for destroying or reducing the number of disease or other harmful microorganisms on a variety of surfaces contaminated therewith thereby essentially eliminating or significantly reducing the potential for spreading diseases associated with the microorganisms through contact with the contaminated surfaces.

DETAILED DESCRIPTION INCLUSIVE OF THE PREFERRED EMBODIMENTS

The compositions of the invention are comprised of three essential ingredients: ethyl alcohol, benzyl alcohol and water, the latter being preponderant. Additionally the compositions may contain other ingredients more fully described hereinbelow.

The concentration in the composition of ethyl alcohol is from about 10 to about 30 weight-percent, preferably from about 19 to about 23 weight-percent, and of benzyl alcohol is from about 2 to about 5 weight-percent. More preferably the concentration of ethyl alcohol is from about 19 to about 21 weight-percent and of benzyl alcohol is from about 3 to about 5 weight-percent.

The major component of the compositions of the invention is water, the concentration of which, based on the total weight of the three essential ingredients, ranges from about 65 to about 88 weight-percent.

One or more other ingredients may optionally be included in the compositions of the invention in order to provide aesthetic or other beneficial properties thereto. Such optional ingredients are, for example, additional antimicrobial agents, deodorizers, emulsifiers, solubilizers, corrosion inhibitors when the compositions are packaged in metal containers, e.g., aerosol containers, and solvents, the only requirement being that for any particular composition such optional ingredients be compatible with the other ingredients present therein.

By way of example, optional ingredients which may be incorporated include the following:

Antimicrobials—phenolic compounds such as o-phenylphenol, o-benzyl-p-chlorophenol and 4-tert-amylphenol; and quaternary ammonium compounds such as alkyl dimethyl benzyl ammonium chloride, octyl decyl dimethyl ammonium chloride, dioctyl dimethyl ammonium chloride, didecyl dimethyl ammonium chloride and alkyl dimethyl benzyl ammonium saccharinate.

Deodorizer—N-alkyl-N-ethylmorpolinium ethyl sulfate.

Emulsifier/Solubilizer—lauryl dimethyl amine oxide, polyoxypropylen,epolyoxyethylene block copolymer and anionic, cationic and nonionic surfactants.

Corrosion Inhibitor—mono- and triethanolamine, ammonium hydroxide, sodium molybdate, sodium benzoate and tetra sodium ethylenediamine tetraacetate ($Na_4EDTA$).

Solvent—alcohols such as isopropyl alcohol and butyl alcohol, each of which can also contribute to antimicrobial activity.

The amounts of optional ingredients to be employed can readily be determined by one skilled in the art. For example, the phenolic and quaternary ammonium antimicrobial agents generally will not exceed a concentration of about 0.2 percent by weight.

The compositions of the invention may be formulated with conventional propellants for dispensing as aerosols from conventional pressurized containers. Propellants which may be used are well known and conventional in the art and include, for example, isobutane, n-butane, propane, dimethyl ether and blends thereof as well as individual or mixtures of chlorofluoro- and/or fluorohydrocarbons. The amount of propellant employed should provide a suitable spray pattern and for essentially complete expulsion of the composition from the aerosol container. The appropriate amount to be used for any particular aerosol propellant system can readily be determined by one skilled in the art. Generally speaking, the amount of a particular propellant employed should provide an internal pressure of from about 30 to about 100 p.s.i.g.

In order to realize the full antimicrobial potential of the compositions of the invention, the contact time of the composition with the microorganism should be at least about 10 minutes.

The compositions can be packaged in conventional, ready-to-use dispensing systems. Thus they can be packaged in aerosol form in conventional aerosol containers or in liquid form in trigger pumps spray bottles and squeeze bottles. They can also be impregnated into towelettes and packaged individually or packaged in bulk form for individual dispensing.

The compositions can be prepared by entirely conventional procedures, no special techniques being required. They are conveniently prepared by adding the ethyl alcohol and the benzyl alcohol to water with mixing followed by any optional ingredients.

The compositions of the invention are illustrated by examples of specific formulations described below without, however, being limited thereto. The concentration of ethyl alcohol in all formulations is based on 100% active. Deionized water was employed in all formulations.

| Example | Ingredient (% by weight) | | |
|---|---|---|---|
| | Ethyl Alcohol | Benzyl Alcohol | Water |
| 1 | 10 | 2 | 88 |
| 2 | 10 | 3 | 87 |
| 3 | 10 | 3.5 | 86.5 |
| 4 | 10 | 4 | 86 |
| 5 | 20 | 2 | 78 |
| 6 | 20 | 3 | 77 |
| 7 | 20 | 4 | 76 |
| 8 | 25 | 2 | 73 |
| 9 | 30 | 3 | 67 |
| 10 | 30 | 4 | 66 |

The compositions of Examples 2,3,4,6 and 8 were tested for antiviral activity against Rhinovirus Type 39 and of Examples 1,2,5,7,9 and 10 for antibacterial activity against Staphylococcus aureus (ATCC 6538) using test methods I and II respectively as follows:

METHOD I

The virus stock was propagated in a continuous line of HeLa(Ohio) cells, and generally contained $log_{10}$ 6.0 $TCID_{50}$/ml. For testing, 0.2 ml of virus stock (containing 10% inactivated fetal calf serum (IFCS)) is spread over the surface of a 60 mm petri plate. The plate is then placed at 35° C. for 45 minutes to dry the inoculum to a uniform film. The test agent (2.0 ml) is then applied to the virus film and allowed to remain in contact, at room temperature, for 10 minutes. After the 10 minute contact time, serial tenfold dilutions are made in assay medium (BME+2% IFCS) and 0.2 ml of each dilution of virus/test agent is then placed into each of four separate wells of MRC-5 cells (grown in BME+2% IFCS). The assay plates are incubated at 33° C. for 10-14 days, with media changes every 3-4 days. Plates are scored for characteristic viral cytopathic effect (cellular rounding and degeneration).

METHOD II

Horse serum is added to a culture of the bacteria to achieve a final concentration of 5% and 0.1 ml of this bacterial suspension is inoculated onto a glass petri plate. The inoculum is spread into a 0.5 inch diameter circle and allowed to dry for 30 to 40 minutes at 37° C. and treated with 1.0 ml of the test agent. After 10 minutes contact time, 9 ml of letheen broth is added to the plate and the surface of the plate is swabbed to loosen any remaining bacteria. Serial dilutions of the test sample are made and plated out to $10^{-1}$, $10^{-3}$, and $10^{-5}$. The test agent is treated in duplicate at each dilution. The assay plates are incubated for 48 to 72 hours at 37° C., the number of colonies at each dilution are counted and the average of the number of colonies from the duplicate tests is calculated for each dilution.

The results of the tests against Rhinovirus Type 39 and Staphylococcus aureus, expressed in terms of logs of inactivation of Rhinovirus Type 39 and Staphylococcus aureus where log 1 or greater represents 90% or greater kill of the microorganism, log 3 or greater representing a kill of 99.9% or greater, are given in Table A.

TABLE A

| Composition | Logs of Inactivation | |
|---|---|---|
| | Staph. aureus | Rhinovirus Type 39 |
| Example 1 | 3.78 | |
| Example 2 | 5.02[a] | ≦1.83 |
| Example 3 | | 2.67 |

TABLE A-continued

| Composition | Logs of Inactivation | |
|---|---|---|
| | Staph. aureus | Rhinovirus Type 39 |
| Example 4 | | 3.33 |
| Example 5 | 5.02$^a$ | |
| Example 6 | | 3.92 |
| Example 7 | 5.02$^a$ | |
| Example 8 | | ≦2.0 |
| Example 9 | 5.43$^b$ | |
| Example 10 | 5.02$^a$ | |

$^a$In Method II, the maximum log of inactivation which could be determined in this particular experiment was 5.02. Thus the log value actually may be higher than indicated.
$^b$This is the result obtained in a repeat test; in the first test a log of inactivation of 4.28 was obtained but this result is believed to be due to experimental error.

Compositions consisting of 2,3 and 4 weight-percent benzyl alcohol in water and 10, 20 and 30 weight-percent ethyl alcohol in water were tested for antiviral and antibacterial activity against Rhinovirus Type 39 and Staphylococcus aureus (ATCC 6538) using the test procedures of Methods I and II described hereinbefore. The results of these tests, expressed as logs of inactivation, are given in Table B.

TABLE B

| Composition | Logs of Inactivation | |
|---|---|---|
| | Staph. aureus | Rhinovirus Type 39 |
| 2% Benzyl alcohol in water | 0.89 | 0.17 |
| 3% Benzyl alcohol in water | 5.02$^a$ | 0.5 |
| 4% Benzyl alcohol in water | 4.37 | ≦2.0 |
| 10% Ethyl alcohol in water | 0 | 1.0 |
| 20% Ethyl alcohol in water | 0 | 1.17 |
| 30% Ethyl alcohol in water | 0.72 | 1.89 |

$^a$see footnote $^a$, Table A

A comparison of the test results in Tables A and B shows that the combination of ethyl alcohol and benzyl alcohol in the compositions of the invention can provide antiviral activity against Rhinovirus Type 39 and antibacterial activity against Staphylococcus aureus the total effect of which is greater than the sum of the two effects taken independently. This is best demonstrated in the case of Staphylococcus aureus by Examples 1,5 and 7 where the total effect in logs of inactivation versus the additive effects is respectively 3.78 v. 0.89, 5.02 v. 0.89 and 5.02 v. 4.37; and in the case of Rhinovirus Type 39 by Examples 2,4 and 6 where the total effects versus the additive effect is respectively 1.83 v. 1.5, 3.33 v. ≦3.0 and 3.92 v. 1.67.

The following compositions were formulated as concentrates for aerosol dispensing.

| Ingredient | % by Weight Example: | | | |
|---|---|---|---|---|
| | 11 | 12 | 13 | 14 |
| Ethyl alcohol | 20.00 | 20.00 | 19.40 | 22.70 |
| Benzyl alcohol | 4.00 | 4.00 | 5.00 | 2.00 |
| o-Phenylphenol | 0.20 | — | — | 0.10 |
| Quaternary ammonium compound | — | 0.05$^a$ | — | — |
| Sodium molybdate | 0.14 | 0.14 | 0.14 | 0.14 |
| Ammonium hydroxide (28%) | — | — | 0.05 | 0.05 |
| Water | | q. s. to 100% | | |

$^a$0.02 weight % Cyncal 80% (Hilton-Davis) (alkyl dimethyl benzyl ammonium chloride wherein alkyl represents 50% $C_{14}H_{29}$, 40% $C_{12}H_{25}$ and 10% $C_{16}H_{33}$); and 0.03 weight % BTC 818 (Stepan Chemical Company) (octyl decyl dimethyl ammonium chloride (25%), dioctyl dimethyl ammonium chloride (12.5%) and didecyl dimethyl ammonium chloride (12.5%)).

The compositions of Examples 11,12,13, and 14 were formulated and packaged for dispensing as aerosols (Examples 11A,12A,13A and 14A respectively). In each case the concentrate consisted of 71 percent by weight of the composition and 29 percent by weight of a hydrocarbon propellant consisting of 80 parts of isobutane and 20 parts of propane.

The aerosol formulations of Examples 11A,12A, 13A and 14A were tested for antimicrobial activity against Staphylococcus aureus (ATCC 6538) and Pseudomonas aeruginosa (ATCC 15442) in the AOAC germicidal spray test (Official Methods of Analysis of the AOAC, 14th ed., 1984, page 71). Thirty slides were tested for bacterial growth per sample per microorganism. The test results, expressed in terms of the number of slides of 30 slides showing bacterial growth, are given in Table C.

TABLE C

| Microorganism | Example: | | | |
|---|---|---|---|---|
| | 11A | 12A | 13A | 14A |
| Staph. aureus | 0/30 | 0/30 | 0/30 | 1/30 |
| Ps. aeruginosa | 0/30 | 1/30 | 0/30 | 0/30 |

The results in Table C demonstrate the antimicrobial effectiveness of the aerosol formulations of Examples 11A,12A, 13A and 14A against Staphylococcus aureus and Pseudomonas aeruginosa.

The aerosol formulations of Examples 11A,12A,13A and 14A were tested against Rhinovirus Type 39 using the following test method:

METHOD III

The virus stock was propagated in a continuous line of HeLa (Ohio) cells, and generally contained $\log_{10}$ 6.0 $TCID_{50}$ per 0.2 ml. For testing, 0.2 ml of virus (containing 5% inactivated newborn calf serum (INCS)) is spread over the surface of a 60 mm petri plate. The plate is then placed at 35° C. for 45 minutes to dry the inoculum to a uniform film. The spray can containing the test agent is held 6–8" from the surface of the plate at an angle of 45°, and the spray is expelled for 3 seconds (2 ml expelled volume). After a 10-minute contact time, serial tenfold dilutions of the treated virus are carried out in growth medium (EMEM+5% INCS). Growth medium is removed from the wells of 12 well assay plates containing subconfluent HeLa (Ohio) cells, and replaced by 2 ml of maintenance medium (EMEM+2% INCS). A 0.2-ml aliquot of each virus/test agent is then placed into each of four separate wells. The assay plates are incubated at 33° C. for 10–14 days, with media changes every 3–4 days. Virus controls are carried out in an identical manner with 2 ml of serum-free EMEM applied to the virus film in place of the spray treatment. Cytotoxicity controls are carried out by repeating the above procedure with 0.2 ml of growth medium as the initial inoculum. Plates are scored for characteristic viral cytopathic effect (cellular rounding and degeneration).

The results of the antiviral test, expressed as logs of inactivation and percent kill of the microorganism, are given in Table D.

TABLE D

| Example | % Kill | Logs of Inactivation |
|---|---|---|
| 11A | >99.99 | ≧4 |
| 12A | >99.9 | ≧3 |
| 13A | >99.99 | ≧4 |
| 14A | >99.9 | ≧3 |

The results in Table D demonstrate the antiviral effectiveness of the aerosol formulations of Examples 11A, 12A, 13A and 14A against Rhinovirus Type 39.

Compositions of the invention were formulated as concentrates for aerosol dispensing (Examples 15 and 16) and for pump-spray dispensing (Examples 17 and 18) as follows:

| | % by Weight Example: | | | |
|---|---|---|---|---|
| Ingredient | 15 | 16 | 17 | 18 |
| Ethyl alcohol | 21.00 | 20.00 | 19.01 | 19.01 |
| Benzyl alcohol | 3.00 | 4.00 | 3.0 | 3.0 |
| o-Phenylphenol | 0.10 | — | 0.075 | — |
| Quaternary ammonium compound | — | 0.05[a] | — | 0.05[a] |
| N-Alkyl-n-ethylmorpholinium ethyl sulfate (35%)[b] | 0.17 | 0.17 | 0.12 | 0.12 |
| Lauryl dimethyl amine oxide (40%)[c] | — | — | 0.2 | 0.2 |
| Triethanolamine (99%) | — | — | 0.2 | 0.2 |
| Polyoxypropylene-polyoxyethylene block copolymer[d] | — | — | 0.75 | 0.75 |
| Sodium benzoate | 0.30 | 0.30 | — | — |
| Ammonium hydroxide (28%) | 0.05 | 0.035 | 0.1 | 0.1 |
| Fragrance | 0.14 | 0.14 | 0.12 | 0.12 |
| Water | q. s. to 100% | | | |

[a]0.02 weight percent of Cyncal 80%, and 0.03 weight % of BTC 818 [see footnote [a], Examples 11-14].
[b]Atlas G-271 (ICI Americas); CTFA name: soyaethyl morpholinium ethosulfate.
[c]Ammonyx DMCD-40 (Stepan Chemical Company); CTFA name; lauramine oxide.
[d]Pluronic F-127 (BASF-Wyandotte); CTFA name: Poloxamer 407.

The compositions of Examples 15 and 16 were formulated and packaged for dispensing as aerosols (Examples 15A and 16A respectively). In each case the concentrate consisted of 71 percent by weight of the composition and 29 percent by weight of a hydrocarbon propellant consisting of 80 parts of isobutane and 20 parts of propane.

The aerosol formulations of Examples 15A and 16A and the compositions of Examples 17 and 18 were tested for antimicrobial activity by standard methods. In the case of bacteria and fungi, the formulations were tested in the AOAC germicidal spray test (Official Methods of Analysis of the AOAC, 14 ed., 1984, page 71). In the case of viruses, testing was performed using Method I described hereinbefore except that for each virus tested, the appropriate host cell line, assay medium and temperature were employed as follows:

| Virus | Host Cell | Medium | Temp (C.) |
|---|---|---|---|
| Rhinovirus Type 39 | MRC-5 | BME + 2% IFCS | 33° |
| Herpes Simplex 1 & 2 | Vero | 199 + 2% IFCS | 37° |
| Vaccinia | Vero | 199 + 2% IFCS | 37° |
| Adenovirus Type 2 | 293 | 199 + 2% IFCS | 37° |
| Respiratory Syncytial | HEt-2 | 199 + 2% IFCS | 37° |
| Influenza A2 & B | MDCK | 199 + 10 μg/ml trypsin | 37° |
| Human Rotavirus | MA-104 | 199 + 5 μg/ml trypsin | 37° |

These tests showed that the aerosol formulations of Examples 15A and 16A and the compositions of Examples 17 and 18 provided greater than 99.9% kill in each case against the following microorganisms:

| Viruses | Bacteria |
|---|---|
| Rhinovirus Type 39 | *Pseudomonas aeruginosa* |

-continued

| | |
|---|---|
| Herpes Simplex 1 & 2 | *Staphylococcus aureus* |
| Human Rotavirus | *Salmonella choleraesuis* |
| Respiratory Syncytial | |
| Influenza A2 & B | |
| Adenovirus Type 2 | |
| Vaccinia | |
| Fungi | |
| *Aspergillus niger* | |
| *Trichophyton mentagrophytes* | |

The composition of Example 17 also was shown to provide greater than 99.9% kill of Mycobacterium tuberculosis var. bovis when tested by the AOAC tuberculocidal method (Offical Methods of Analysis of the AOAC, 14th ed., 1984, page 73).

What is claimed is:

1. An aqueous antimicrobial composition comprising from about 10 to about 30% by weight of ethyl alcohol, from about 2 to about 5% by weight of benzyl alcohol and the remainder to 100% water.

2. A composition according to claim 1 wherein the amount of ethyl alcohol is from about 19 to about 23% by weight.

3. A composition according to claim 2 wherein the amount of ethyl alcohol is from about 19 to about 21% by weight and of benzyl alcohol is from about 3 to about 5 percent by weight.

4. A composition according to claim 1 which includes up to about 0.2% by weight of an antimicrobial agent selected from the group consisting of phenolic compounds and quaternary ammonium compounds.

5. A composition according to claim 4 wherein the antimicrobial agent is o-phenylphenol.

6. A composition according to claim 5 wherein the o-phenylphenol is present in an amount of from about 0.07 to about 0.2 percent by weight.

7. A composition according to claim 3 comprising about 21% by weight of ethyl alcohol, about 3% by weight of benzyl alcohol, about 0.10% by weight of o-phenylphenol and the remainder to 100% water.

8. A composition according to claim 7 consisting essentially of about 21.0% by weight of ethyl alcohol, about 3.0% by weight of benzyl alcohol, about 0.1% by weight of o-phenylphenol, about 0.06% by weight of soyaethyl morpholinium ethyl sulfate, about 0.3% by weight of sodium benzoate, about 0.014% by weight of ammonium hydroxide and the remainder to 100% water.

9. A composition according to claim 3 comprising about 19.0% by weight of ethyl alcohol, about 3.0% by weight of benzyl alcohol and the remainder to 100% water.

10. A composition according to claim 9 consisting essentially of about 19.0% by weight of ethyl alcohol, about 3.0% by weight of benzyl alcohol, about 0.075% by weight of o-phenylphenol, about 0.042% by weight of soyaethyl morpholinium ethosulfate, about 0.08% by weight of lauryl dimethyl amine oxide, about 0.2% by weight of triethanolamine, about 0.75% by weight of poloxamer 407, about 0.028% by weight of ammonium hydroxide and the remainder to 100% water.

11. A method for destroying or reducing the number of harmful microbes on an inanimate surface contaminated therewith which comprises contacting the microbes with an antimicrobially effective amount of the composition of claim 1.

12. A method for destroying or reducing the number of harmful microbes on an inanimate surface contaminated therewith which comprises contacting the microbes with an antimicrobially effective amount of the composition of claim 3.

13. A method for destroying or reducing the number of harmful microbes on an inanimate surface contaminated therewith which comprises contacting the microbes with an antimicrobially effective amount of the composition according to claim 8.

14. A method for destroying or reducing the number of harmful microbes on an inanimate surface contaminated therewith which comprises contacting the microbes with an antimicrobially effective amount of the composition according to claim 10.

15. A method for killing microbes which comprises contacting the microbes with an antimicrobially effective amount of the composition according to claim 1.

16. A method for killing microbes which comprises contacting the microbes with an antimicrobially effective amount of the composition according to claim 3.

17. A method for killing microbes which comprises contacting the microbes with an antimicrobially effective amount of the composition according to claim 8.

18. A method for killing microbes which comprises contacting the microbes with an antimicrobially effective amount of the composition according to claim 10.

* * * * *